United States Patent [19]
Portilla et al.

[11] Patent Number: 6,004,809
[45] Date of Patent: Dec. 21, 1999

[54] CALCIUM-INDEPENDENT PHOSPHOLIPASE $A_2$

[75] Inventors: Didier Portilla; Sudhir V. Shah, both of Little Rock, Ark.

[73] Assignee: The Board of Trustees of the University of Arkansas, Little Rock, Ark.

[21] Appl. No.: 09/093,142

[22] Filed: Jun. 8, 1998

Related U.S. Application Data

[62] Division of application No. 08/542,071, Oct. 12, 1995, Pat. No. 5,773,276.

[51] Int. Cl.⁶ .............................. C12N 5/12; C07K 16/40; A61K 39/395; G01N 33/53
[52] U.S. Cl. .................. 435/338; 435/7.1; 435/7.21; 435/326; 435/331; 530/387.1; 530/387.9; 530/388.1; 530/388.2; 530/388.26; 530/388.85; 530/389.1; 530/391.3
[58] Field of Search ........................... 530/388.26, 387.1, 530/389.1, 391.3, 391.7, 387.9, 388.1, 388.2, 388.85; 424/139.1, 146.1; 435/7.1, 7.21, 326, 344.1, 331, 338; 436/501

[56] References Cited

PUBLICATIONS

Dai an Portilla (J. Am. Soc. Nephrology 5(3):895 Presented Oct. 26–29, 1994).

Portilla and Dai, J. Biol. Chem 271 (26): 15451–1547, 1996.

*Primary Examiner*—Nancy A Johnson
*Attorney, Agent, or Firm*—Benjamin Aaron Adler

[57] ABSTRACT

The present invention provides a substantially pure phopholipase $A_2$ protein isolated and purified from rabbit kidney cortex, having a molecular weight of 28 kDa as determined by SDS-PAGE, is calcium independent, is cytosolic, has a specific activity of approximately 1.2 $\mu$mol/mg protein/minute and a pH optimum of approximately 7.5 and exhibits a preferential hydrolysis toward sn-2 fatty acid from diradylglycerophospholipids. Also provided are a first monoclonal antibody that specifically binds to the protein of claim 1 various methods of using, inhibiting or measuring said protein.

7 Claims, 9 Drawing Sheets

SEQUENCE LISTING (1) GENERAL INFORMATION:

(iii) NUMBER OF SEQUENCES:  3

(2) INFORMATION FOR SEQ ID NO:1:

(i) SEQUENCE CHARACTERISTICS:
        (A) LENGTH:  13 amino acids
        (B) TYPE:  amino acid
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal fragment (xi) SEQUENCE DESCRIPTION:SEQ ID NO:    1:

Ala Ser Phe Pro Gln Gly Pro Ile Ser Gly Ala Asn Arg
                5                   10

(2) INFORMATION FOR SEQ ID NO:2:

(i) SEQUENCE CHARACTERISTICS:
        (A) LENGTH:  11 amino acids
        (B) TYPE:  amino acid
        (D) TOPOLOGY:  linear (ii) MOLECULE TYPE:
        (A) DESCRIPTION:  peptide (iii) HYPOTHETICAL:  no (iv) ANTI-SENSE:  no (v) FRAGMENT TYPE:  internal fragment (xi) SEQUENCE DESCRIPTION:SEQ ID NO:    2:

Thr Leu Val Asn Pro Ala Asn Val Thr Phe Lys
                5                   10

```
(2) INFORMATION FOR SEQ ID NO:3:

(i) SEQUENCE CHARACTERISTICS:
        (A) LENGTH:  6 amino acids
        (B) TYPE:    amino acid
        (D) TOPOLOGY: linear (ii) MOLECULE TYPE:
        (A) DESCRIPTION:  peptide (iii) HYPOTHETICAL:  no (iv) ANTI-SENSE:  no (v) FRAGMENT TYPE:  internal fragment (xi) SEQUENCE DESCRIPTION:SEQ ID NO:   3:

Ala Leu Ile Asp Gln Glu
```

CALCIUM-INDEPENDENT PHOSPHOLIPASE A$_2$

This is a divisional application of U.S. Ser. No. 08/542,071 filed on Oct. 12, 1995, now U.S. Pat. No. 5,773,276.

BACKGROUND OF THE INVENTION

1. Field of the Invention

The present invention relates generally to the fields of nephrology and protein chemistry. More specifically, the present invention relates to the isolation and purification of a novel calcium-independent phospholipase A$_2$.

2. Description of the Related Art

Phospholipase A$_2$ (PLA$_2$) enzymes (EC 3.1.1.4) are a group of lipolytic enzymes that catalyze the hydrolysis of the acyl ester bond at the sn-2 position of glycerophospholipids resulting in the release of arachidonic acid from membrane phospholipids and the production of lysophospholipids (1,2). Mammalian phospholipase A$_2$s are structurally a diverse group of enzymes which include the calcium-dependent secreted phospholipase A$_2$ (sPLA$_2$) forms characterized by their low molecular weight, high disulfide bond content and an absolute requirement of calcium during hydrolysis (3,4). A second recently identified group of intracellular cytosolic phospholipase A$_2$s comprise the low-calcium-requiring 85 kDa cytosolic phospholipase A$_2$ (cPLA$_2$) (5,6), and two new calcium-independent phospholipase A$_2$ enzymes, a 40 kDa plasmalogen selective calcium-independent phospholipase A$_2$ purified from canine myocardium (7–9) and a 80 kDa cytosolic calcium-independent phospholipase A$_2$ recently purified from the macrophage-like cell line P388D1 (10–11 ).

In kidney and heart tissue (12–14), early studies have demonstrated that activation of intracellular phospholipase A$_2$ represents an important mechanism leading to the development of metabolic alterations which precede cell death during ischemia. Recent observations have demonstrated that the majority of measurable phospholipase A$_2$ activity in freshly isolated rabbit proximal tubules was present in the cytosolic compartment and was calcium-independent and arachidonate-selective (14). These studies also suggest that activation of this calcium-independent phospholipase A$_2$ enzyme during hypoxia precedes cell death and is accompanied by hydrolysis of endogenous proximal tubule plasmalogen substrates leading to generation of arachidonic acid and accompanying phospholipid catabolism (15). Since the release of arachidonic acid and the concomitant accumulation of amphiphilic products derived from phospholipase A$_2$ activation such as lysoplasmalogens have been shown to be important modulators of renal NaK-ATPase (16), the isolation and identification of the biochemical mechanisms which regulate the activity of this calcium-independent PLA$_2$ are of obvious importance.

The prior art is deficient in the lack of the purification and characterization of a novel calcium-independent PLA$_2$ from rabbit kidney cortex. The present invention fulfills this longstanding need and desire in the art.

SUMMARY OF THE INVENTION

The present invention describes the 3,200 fold purification of a cytosolic calcium-independent phospholipase A$_2$ to homogeneity from rabbit kidney cortex through sequential column chromatography including anion exchange, hydrophobic interaction, Mono Q, hydroxylapatite, Phenyl sepharose and chromatofocusing FPLC from rabbit kidney cortex. The purified enzyme had a molecular mass of 28 kDa, a unique internal amino acid sequence, possessed a specific activity of 1.2 μmol/mg/min, a pH optimum of 7.5, and exhibits a preferential hydrolysis toward sn-2 fatty acid from diradylglycerophospholipids. The purified polypeptide hydrolyzed plasmenylcholine>phosphatidylcholine glycerophospholipids. The purified polypeptide of the present invention selectively cleaved phospholipids containing arachidonic acid at the sn-2 position in comparison to oleic acid. Antibodies against the purified protein of the present invention precipitated all the soluble calcium-independent phospholipase A$_2$ activity from rabbit kidney cortex. Thus, the present invention demonstrates altogether that there is a novel class of calcium-independent phospholipase A$_2$.

The 28 kDa protein described by the present invention has calcium independent phospholipase A$_2$ activity selective against arachidonylated plasmalogen phospholipid substrates. This enzyme differs from the previously reported calcium-independent phospholipase A$_2$s in that it is not modulated by ATP and that does not require association with a high molecular weight complex to express catalytic activity. Immunoprecipitation and Western blot analysis confirmed the association of a 28 kDa protein with calcium-independent plasmalogen selective phospholipase A$_2$ activity.

In one embodiment of the present invention, there is provided a substantially pure phopholipase A$_2$ protein isolated and purified from rabbit kidney cortex, having a molecular weight of 28 kDa as determined by SDS-PAGE, is calcium independent, is cytosolic, has an internal sequence shown by the following three peptides:

peptide 1: ASFPQGPISGANR (SEQ ID No. 1);
peptide 2: TLVNPANVTFK (SEQ ID No. 2); and
peptide 3: ALIDQE (SEQ ID No. 3); and
exhibits a preferential hydrolysis toward sn-2 fatty acid from diradylglycerophospholipids.

In another embodiment of the present invention, there is provided a pharmaceutical composition, comprising an inhibitor of the protein of the present invention and a pharmaceutically acceptable carrier.

In yet another embodiment of the present invention, there is provided a antibody that specifically binds to the protein of the present invention.

In still yet another embodiment of the present invention, there is provided a kit for immunodection, comprising: a container means; a first monoclonal antibody that specifically binds to the protein of claim 1; and an immunodetection reagent.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the typical column chromatography profiles of the calcium-independent phospholipase A$_2$ from rabbit kidney cortex following: Phenyl Sepharose CL-4B separation (FIG. 1A); Mono Q FPLC separation (FIG. 1B); hydroxyapatite FPLC separation (FIG. 1C); Phenyl Superose FPLC (FIG. 1D); and chromatofocusing FPLC (FIG. 1E).

DETAILED DESCRIPTION OF THE INVENTION

The present invention is directed to a substantially pure phopholipase $A_2$ protein isolated and purified from rabbit kidney cortex, having a molecular weight of 28 kDa as determined by SDS-PAGE, is calcium independent, is cytosolic, has an internal sequence shown by the following three peptides:

peptide 1: ASFPQGPISGANR (SEQ ID No. 1);
peptide 2: TLVNPANVTFK (SEQ ID No. 2); and
peptide 3: ALIDQE (SEQ ID No. 3); and
exhibits a preferential hydrolysis toward sn-2 fatty acid from diradylglycerophospholipids.

Moreover, the protein of the present invention has a specific activity of approximately 1.2 µmol/mg protein/minute and a pH optimum of approximately 7.5 and exhibits a preferential hydrolysis toward sn-2 fatty acid from diradylglycerophospholipids. The protein of claim 1, wherein said protein preferentially hydrolyzed plasmenylcholine>phosphatidylcholine glycerophospholipids. Moreover, the protein selectively cleaved phospholipids containing arachidonic acid at the sn-2 position in comparison to oleic acid.

The present invention also provides an antibody that specifically binds to the protein described herein. The antibody may be a monoclonal antibody or a polyclonal antibody. In one embodiment, the antibody is linked to a detectable label. The present invention also provides a hybridoma that produces such a monoclonal or polyclonal antibody.

The present invention also provides a kit for immunodection, comprising: a container means; a first monoclonal antibody that specifically binds to the protein of claim 1; and an immunodetection reagent. Preferably, the immunodetection reagent is a detectable label linked to said first antibody.

It is specifically contemplated that pharmaceutical compositions may be prepared using the novel protein of the present invention. In such a case, the pharmaceutical composition comprises an inhibitor of the novel protein of the present invention and a pharmaceutically acceptable carrier. A person having ordinary skill in this art would readily be able to determine, without undue experimentation, the appropriate dosages and routes of administration of the inhibitors of the novel protein of the present invention.

The following examples are given for the purpose of illustrating various embodiments of the invention and are not meant to limit the present invention in any fashion.

EXAMPLE 1

Materials

Radioactive lipids were purchased from New England Nuclear Research Products (Boston Mass.). 1-O-hexadecanoyl-2-cis-octadec-[9,10-$^3$H]enoyl-sn-glycero-3-phosphocholine ($^3$H-labeled plasmenylcholine) were prepared by dimethylaminopyridine-catalyzed acylation of 1-O-hexadecanoyl-sn-glycero-3-phosphocholine and 1-O-hexadec-1'-enyl-sn-glycero-3-phosphocholine, respectively using [$^3$H] oleic anhydride as previously described (7,14). To compare activity against arachidonic acid labeled phosphatidylcholine substrate, commercially available 1-palmitoyl-2-[$^{14}$C]-arachidonyl-sn-glycero-3-phosphocholine was used. The Phenyl Sepharose CL-4B, Mono Q HR 10/10 Mono P Chromatofocusing and FPLC system used were from Pharmacia LKB Biotechnology Inc. Hydroxylapatite (BioGel HTP) and CM Affi-Gel Blue gel were purchased from BioRad.

EXAMPLE 2

Phospholipase $A_2$ Assay

Phospholipase $A_2$ activity was assessed by incubating enzyme with the indicated concentration of radiolabeled phospholipid which was introduced by ethanol injection of 10 µl in assay buffer with 10 µM sn-2 radiolabeled choline glycerophospholipid (specific activity 40 Ci/mol). The final assay buffer consisted of 50 mM Tris HCl and 4 mM EGTA pH 7.3, at 37° C. for 15 minutes. All measurements of phospholipase $A_2$ activity were made under initial reaction conditions where the observed rates of fatty acid release were linear with respect to time and protein content. Reactions were quenched by the addition of butanol (100 µL) and radiolabeled products were separated by TLC prior to quantification by scintillation spectrometry as previously described (14).

EXAMPLE 3

Protein Purification

Preparation of homogenate: Twenty frozen rabbit kidneys obtained from PelFreeze (Rogers, Ark.) were thawed in KEI buffer containing 150 mM KC1, 1 mM EDTA-Tris, 25 mM imidazole pH 7.4, 0.1 mM PMSF, 1 µg/ml of pepstatin A and 1.5 µg/ml of leupeptin. The kidney cortices were carefully separated from the medulla and homogenized in KEI buffer using a blender and LSC homogenizer (LH21 Yamamoto) at 900 rpm. The cytosol was prepared by centrifugation at 100,000×g for 60 minutes. The supernatant which was used for the purification was collected and filtered through a glasswool column.

EXAMPLE 4

Ammonium Sulfate Precipitation

Approximately 200 mls of cytosolic fraction was brought to 45% saturation with solid ammonium sulfate. This solution was stirred slowly for 30 minutes and centrifuged at 10,000×g for 20 minutes. The supernatant was discarded and the pellet was resuspended in HIC-buffer (10 mM imidazole 1 mM potassium phosphate 1 mM EDTA-Tris, 0.5 mM triton X-100, 10% glycerol 0.1 mM PMSF, 1 μg/ml pepstatin A and 1.5 μg leupeptin pH 6.8).

EXAMPLE 5
Phenyl Sepharose Column

The sample containing the pellet from the ammonium sulfate precipitation step was directly loaded onto a Phenyl Sepharose CL-4B previously equilibrated with HIC-A buffer (HIC-B plus 0.15 mM ammonium sulfate). After extensively washing with HIC-A buffer the column was developed with HIC-B buffer. The eluant was collected in 10 ml fractions. The active fractions from the Phenyl Sepharose column were pooled and concentrated prior to the next step. The majority of the activity (80%) was collected in the fraction corresponding to low salt buffer without ammonium sulfate.

EXAMPLE 6
CM-Blue Sepharose Column

Sample obtained from the hydrophobic interaction column was directly loaded onto a CM-Blue column which was previously equilibrated with HIC-B buffer. The column was eluted with Buffer C (0.5 M potassium phosphate pH 6.8) and phospholipase $A_2$ activity was obtained in the flow through fraction.

EXAMPLE 7
Mono O FPLC Column

The active fractions eluted from the CM-Blue sepharose column were pooled and adjusted to pH 8.0 with 1M Tris base then loaded onto a Mono Q HR 10/10 FPLC column at 1 ml/min. The Mono Q column was previously equilibrated with buffer consisting of 25 mM Tris, 10 mM KCl, 1 mM potassium phosphate, 0.5 mM Triton X 100, 1 mM DTT, 10% glycerol pH 8.0. After equilibration, the enzyme activity was eluted with a similar buffer containing 1M NaCl. The enzyme was eluted in the first buffer and the active fractions were in the first peak were pooled.

EXAMPLE 8
Hydroxyapatite FPLC

The pooled fractions from the Mono Q column, were loaded onto a hydroxyapaptite FPLC column which was previously equilibrated with a buffer consisting of 25 mM Tris 10 mM KCl, 1 mM potassium phosphate 0.5 mM Triton X 100, 1 mM DTT, 10% glycerol pH 8.0. The column was eluted with a similar buffer but containing 0.5M potassium phosphate in the same buffer. Most of the activity was recovered after elution with the first buffer but a small peak of activity was eluted at 0.5 M potassium phosphate.

EXAMPLE 9
Phenyl Superose HPLC Column

The pooled fractions from the hydroxyapatite column were brought up to 0.2 M ammonium sulfate by the addition of solid ammonium sulfate and pH adjusted to 6.8. The sample was loaded onto a Phenyl Superose HR 5/5 FPLC column. After extensive washing with HIC-A buffer, the majority of phospholipase $A_2$ activity was recovered in the fraction corresponding to 0.1M ammonium sulfate in HIC-B buffer. This fraction was used to determine the pH dependence of phospholipase $A_2$ activity.

EXAMPLE 10
Native Gel Electrophoresis

Native gel electrophoresis was carried out following the method of Kramer (6). Briefly, 6% separating gel pH 7.3 and 4% stacking gel pH 6.8 of polyacrylamide in 40 mM Tris-acetate were casted in BioRad Mini Gel II with 1.5 mm thick spacer and prep-comb. The purified fraction containing phospholipase $A_2$ activity after the hydrophobic interaction column was concentrated with Centri-Prep, Amicon and an aliquot of the preparation corresponding approximately to 20 μg of protein was mixed with 0.2 g of SM-2 BioRad and kept on ice for 2 hours to remove the Triton X-100 in the sample. The detergent-removed sample was directly loaded onto the gel and run in 50 mM Tris-acetate pH 7.3 at 30 mA for 100 minutes at 4° C. A 6 mm wide strip was cut at the middle of the gel then sliced every 2 mm from the top to the bottom and transferred to a mini test tube. After rinsing the slices with running buffer they were incubated overnight on a rotating plate in 150 μl of a buffer containing 4 mM EGTA, 0.5 mM Triton X-100, 0.2 mM ATP and 1 mM DTT pH 7.5. $PLA_2$ activities were measured using 100 μl volume of each sample.

EXAMPLE 11
Chromatofocusing FPLC Column

To determine the pI of purified phospholipase $A_2$ the last step of purification was carried out on a Mono P HR 5/20 column. Prior to loading the sample the column was equilibrated with starting buffer containing 25 mM Bis-Tris, 0.5 mM NP40 and 10% glycerol pH 6.3. the active fraction from the hydrophobic interaction column was extensively dialyzed with the starting buffer and loaded onto the column. The column was eluted with a buffer containing 12.5% polybuffer 74, 0.5 mM NP40, 10% glycerol adjusted to pH 4.0 with HCl at a flow rate of 0.25 ml/min. Forty fractions of 1 ml volume were collected and the pH of each fraction was checked with pH meter at 4° C. Only one remarkable peak of protein in fraction 19 contributed to 90% of the activity and corresponded to a pH 5.5 to 5.6. The other 10% of the activity was found in the flow through fraction.

EXAMPLE 12
Preparation of Polyclonal Antibodies

Immunization was performed by subcutaneous injection of 7 μg of purified phospholipase $A_2$ protein mixed with Titer Max used as a adjuvant at the base of the tail of female BALB/C mice. Two boosting injections with half amount of same antigen in Titer Max were given at an interval of 5 weeks. Preimmunized sera and antisera were collected before each injection.

EXAMPLE 13
Immunoprecipitation of Rabbit Kidney Cytosolic $PLA_2$ Activity

Different amounts of preimmunized sera and antisera from each mouse were diluted 10 and 100 fold with normosaline and incubated with purified phospholipase $A_2$ (active fraction from hydrophobic interaction) on a rotating plate at 4° C. At 1 and 2 hour intervals 10 μg of goat antimouse IgG and 10 μl of slurry of Protein A beads were added respectively to each vial. After overnight incubation the beads were spun down in an Eppendorf centrifuge and an aliquot of the supernatant was used to determine phospholipase $A_2$ activity.

EXAMPLE 14
Sequencing

The 28 kDa protein purified from rabbit kidney cortex was transferred to polyvylidene difluoride membrane and sent to the Harvard Microchemistry Laboratory in Boston, Mass. for determination of the amino acid sequence. Because the amino-terminal residue of the 28 kDa protein was blocked, it was necessary to obtain internal peptide sequence after tryptic peptide digestion. A mass spectrometry chromatogram was obtained to confirm purity of the isolated peptides prior to sequencing.

EXAMPLE 15
Purification of Rabbit Kidney Cytosolic Calcium-independent Phospholipase $A_2$ Since approximately 90% of calcium independent phospholipase $A_2$ activity was present in the cytosol of rabbit kidney cortex when compared to the membrane-associated fraction the purification of this enzyme activity was performed using the soluble fraction of rabbit kidney cortex.

Similar to Dennis et al (10), the inclusion of Triton X-100 (0.5 mM) in the buffers used for the purification helped to stabilize the rabbit kidney calcium-independent phospholipase $A_2$ activity. Cytosolic rabbit kidney calcium-independent phospholipase $A_2$ was purified to homogeneity by sequential hydrophobic interaction, CM-Blue Sepharose affinity chromatography, Mono Q FPLC, Hydroxyapatite FPLC, Phenyl Sepharose FPLC and chromatofocusing. Typical column profiles are shown in FIG. 1, A–E. First, cytosolic fraction was applied to a Phenyl Sepharose CL-4B hydrophobic interaction column and the majority (80–90%) of the phospholipase $A_2$ activity retained by the column was quantitatively eluted by application of a low salt buffer without ammonium sulfate. Since previous studies have identified the potential association of ATP with calcium-independent phospholipase $A_2$, the interaction of calcium-independent $PLA_2$ with various immobilized nucleotide affinity matrices was demonstrated. Kidney calcium-independent phospholipase $A_2$ activity did not bind to ATP-agarose or Blue Sepharose affinity matrices and more than 90% of the activity was recovered in the void volume. Because of the significant amount of protein without phospholipase $A_2$ activity retained by the Blue Sepharose column, this step was used to further purify calcium-independent phospholipase $A_2$ activity after the hydrophobic interaction column.

Figure 1A:
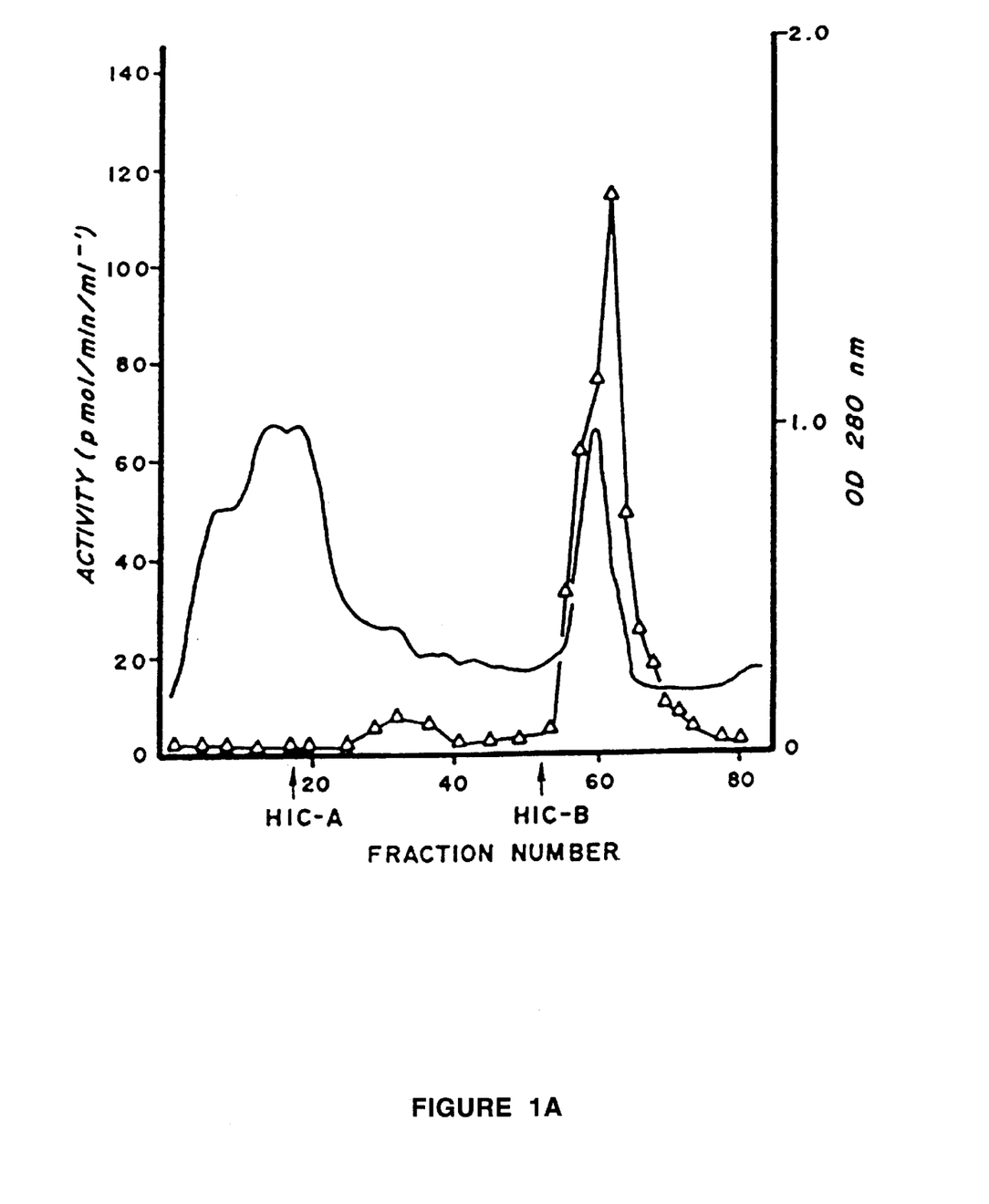
Figure 1B:
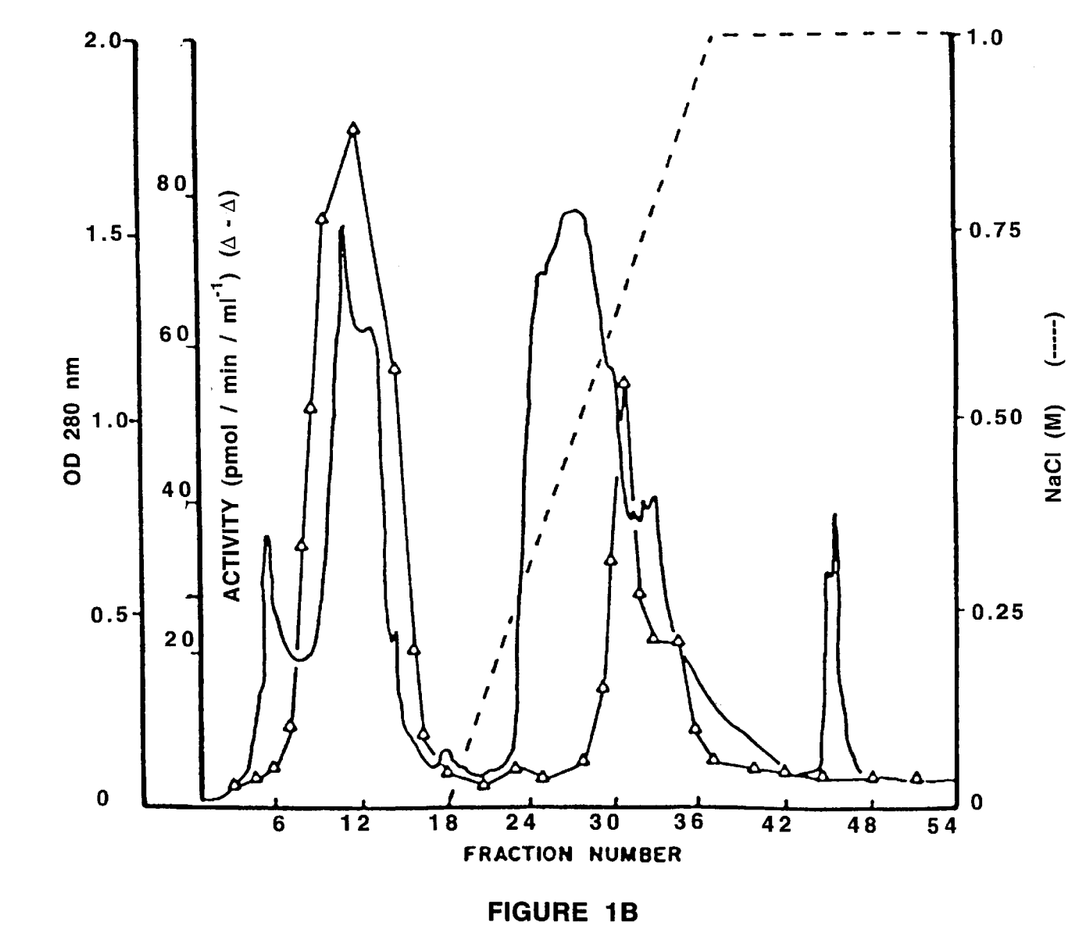
Figure 1C:
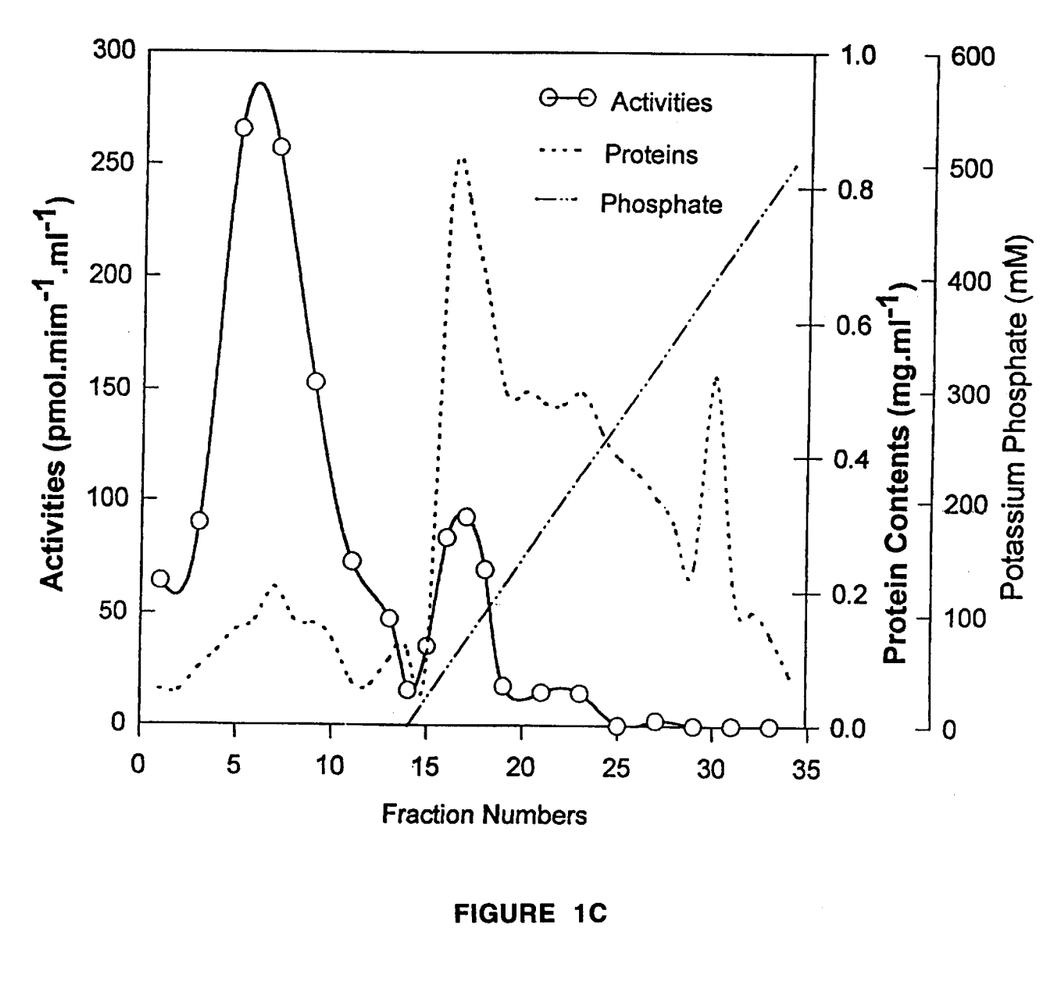
Figure 1D:
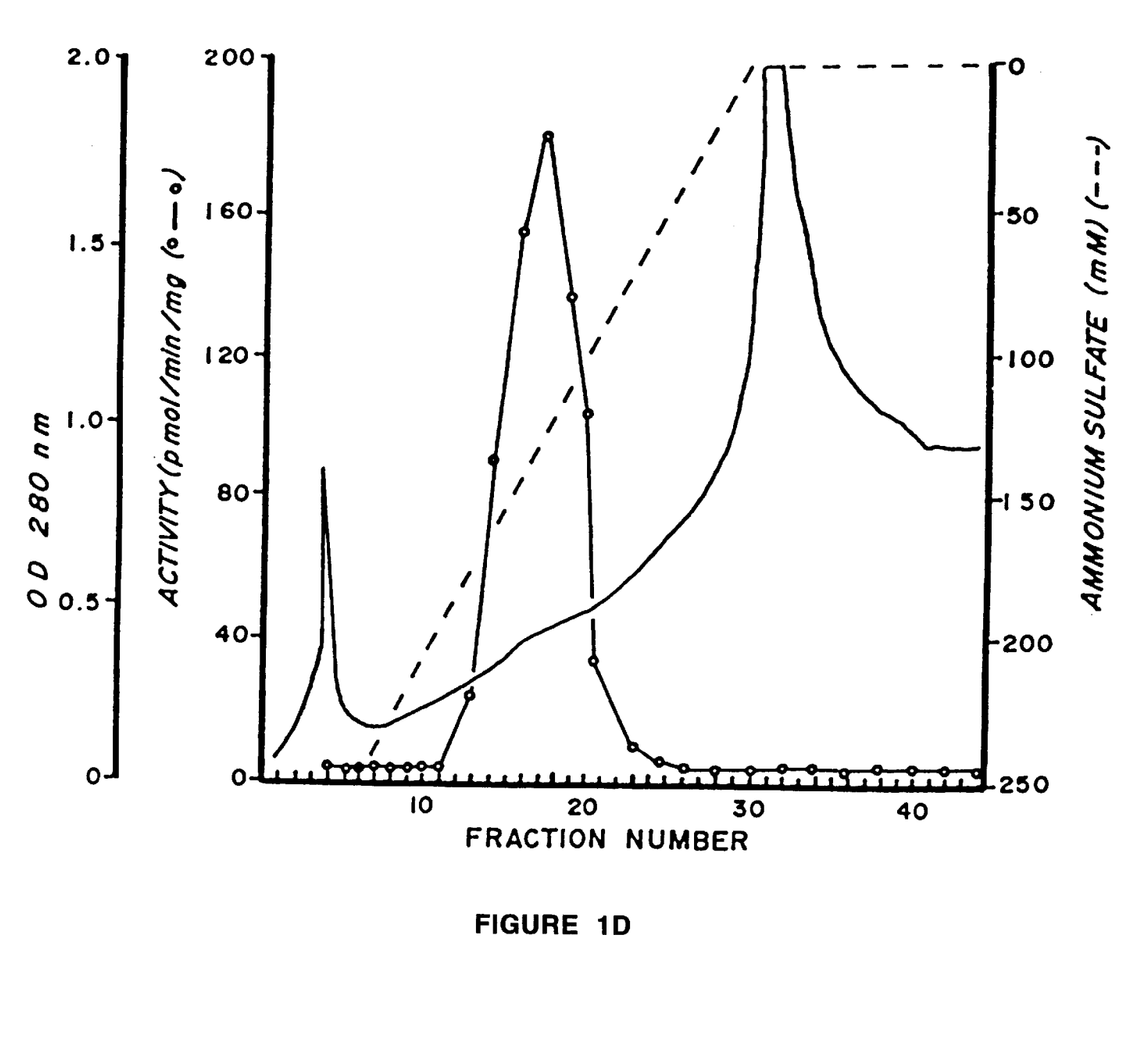
Figure 2:
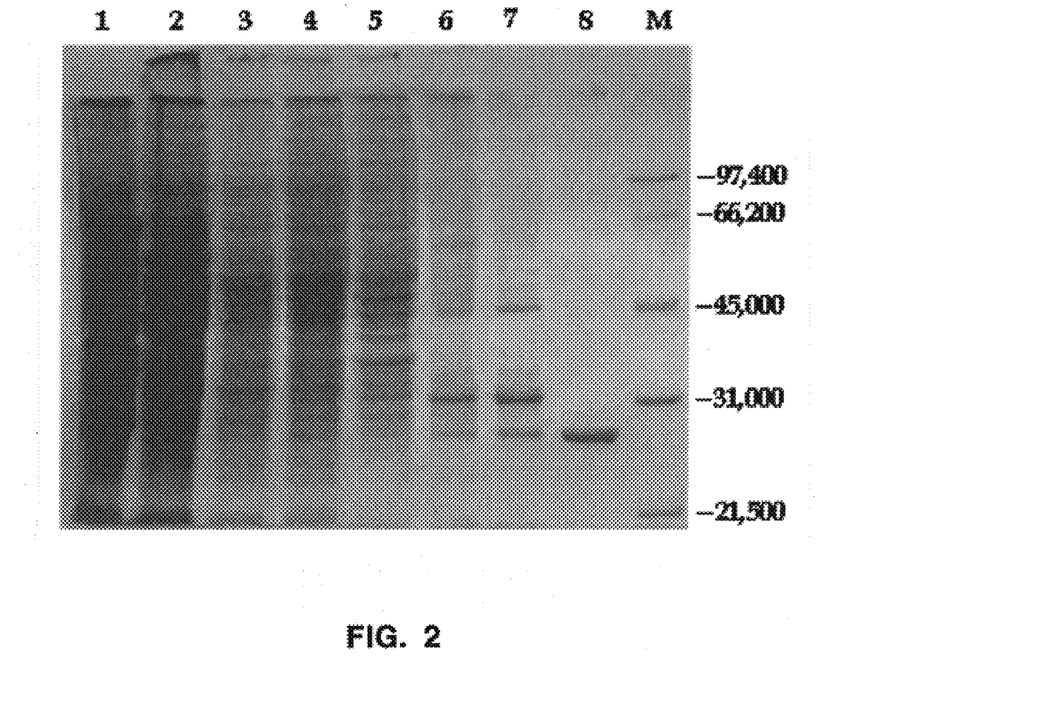
FIG. 2 shows the SDS-PAGE of fractions containing calcium-independent phospholipase $A_2$ activity. 1. soluble fraction, 2. ammonium sulfate precipitation, 3. Phenyl sepharose column, 4. blue sepharose column, 5. anion exchange Mono Q FPLC column, 6 and 7 hydroxyapatite column, 8. phenyl superose hydrophobic interaction column, M corresponds to standard molecular weight markers.

Phospholipase $A_2$ activity was further purified by application of the Blue sepharose eluate onto a FPLC-Mono Q anion exchange column which was subsequently eluted utilizing a continuous NaCl gradient (FIG. 1B). Two major peaks containing calcium-independent phospholipase $A_2$ activity were obtained from the ion exchange column. However the first peak of activity eluted in the void volume contained the majority of calcium-independent phospholipase $A_2$ activity. The dialyzed sample containing this phospholipase $A_2$ activity was loaded onto a FPLC-hydroxyapatite column, and phospholipase $A_2$ activity was eluted with a linear $K[PO_4]$ gradient as described above (FIG. 1C). The peak. containing phospholipase $A_2$ activity was eluted at 10 mM phosphate. This peak was further purified by Phenyl Sepharose hydrophobic interaction. Again phospholipase activity was eluted off this column in a low salt buffer (FIG. 1D). This calcium-independent phospholipase $A_2$ activity was purified over 3,000 fold with a final specific activity roughly of about 1 $\mu$mol/min/mg protein. Assessment of purity was carried out using SDS PAGE under reducing conditions. In every purification, the final fraction containing calcium-independent phospholipase $A_2$ activity obtained from the hydrophobic interaction column was associated displayed a single major band of 28 kDa (FIG. 2).

TABLE I

Purification Table

|  | Total protein (mg) | Specific Activity |
|---|---|---|
| Homogenate | 4537 | 362 pmol/mg/min |
| Ammonium sulfate | 2014 | 394 pmol/mg/min |
| HIC | 628 | 966 pmol/mg/min |
| Blue Sepharose | 483 | 1942 pmol/mg/min |
| Mono Q | 241 | 2386 pmol/mg/min |
| Hydroxyapatite | 23 | 11,367 pmol/mg/min |
| Phenyl sepharose | 0.18 | 1.16 $\mu$mol/mg/min |

Figure 3:
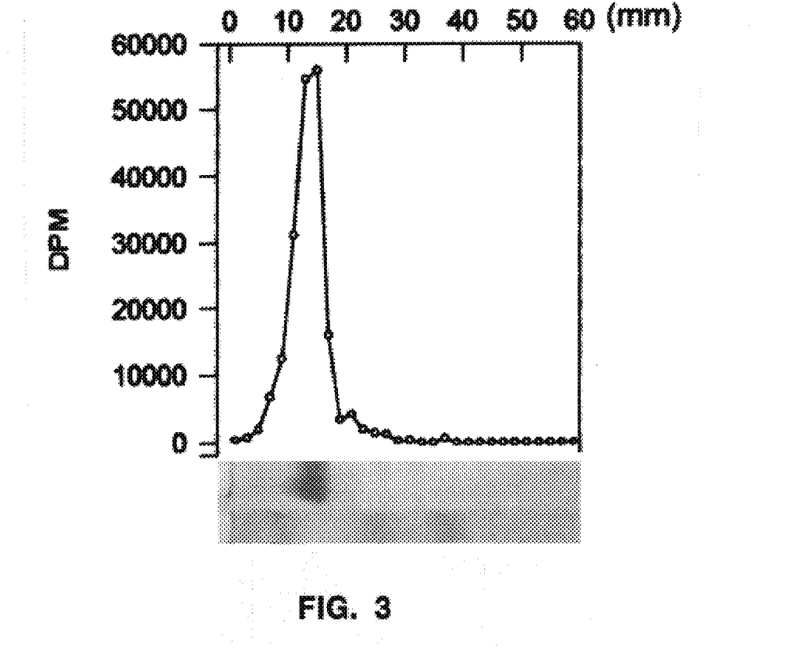
FIG. 3 shows the detection of phospholipase $A_2$ activity after native PAGE of purified phospholipase $A_2$. Aliquots of purified phospholipase $A_2$ (20 µg hydrophobic phenyl superose column) and protein standards were applied in parallel lanes and subjected to electrophoresis under nondenaturing conditions. One lane was sliced into small pieces and phospholipase $A_2$ activity was eluted as described below. The remaining gel was coomassie blue stained.
Figure 4:
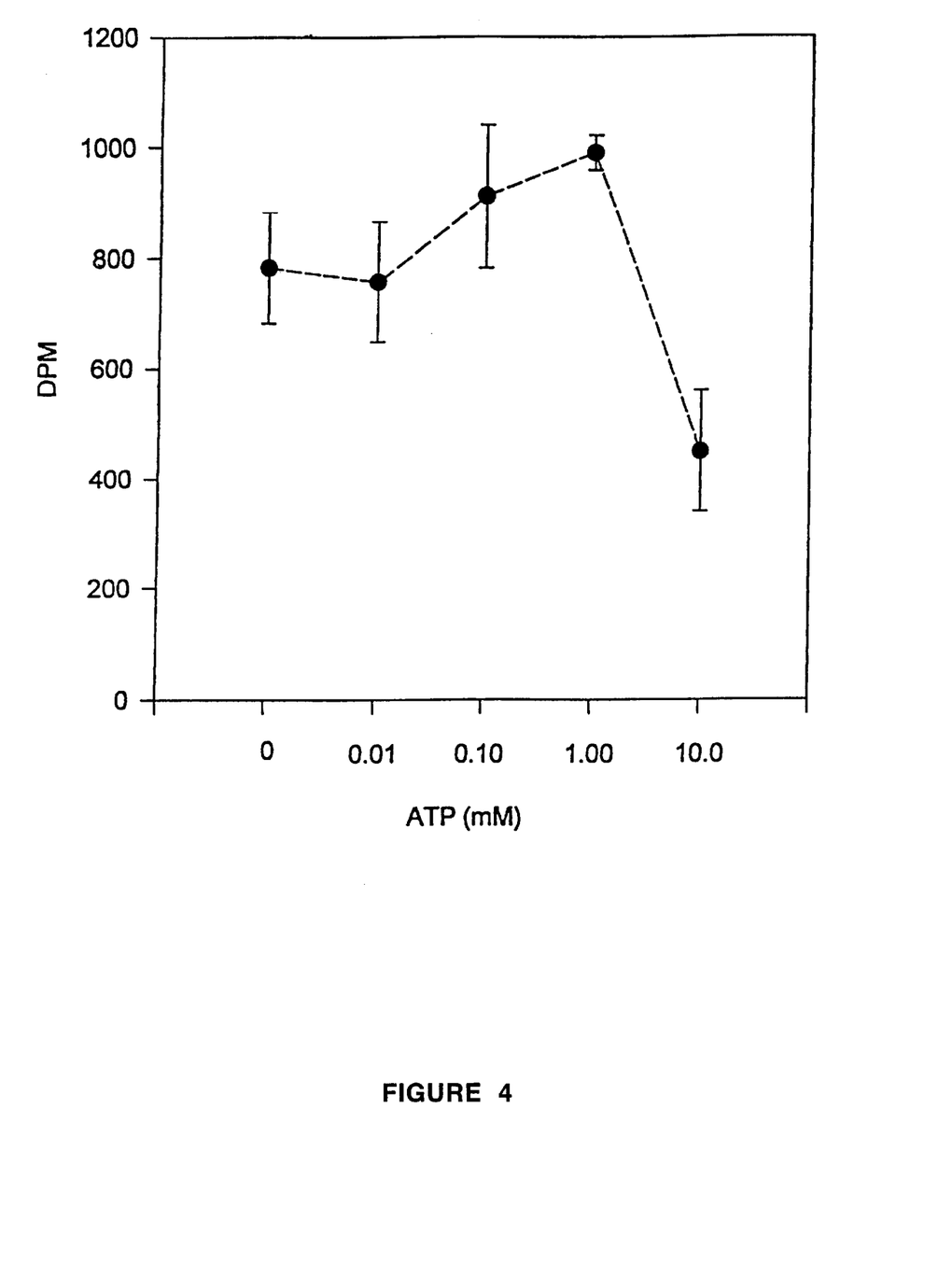
FIG. 4 shows the effects of various concentrations of ATP on calcium-independent phospholipase $A_2$ activity.

EXAMPLE 16
The 28 kDa Protein Purified to Near Homogeneity has Calcium-independent Phospholipase $A_2$ Activity In order to demonstrate that the 28 kDa protein contained phospholipase $A_2$ activity, the final enzyme preparation obtained from the Phenyl Sepharose column was subjected to electrophoresis under native conditions as described above. Approximately 20 $\mu$g of protein were applied to two lanes. The two lanes were cut from the gel. One was stained with Coomassie blue and the other sliced into small pieces, incubated overnight with buffer containing Triton X 100 and assayed for phospholipase $A_2$ activity. Greater than 60–70% of the applied phospholipase $A_2$ activity was recovered and the profile for calcium-independent phospholipase $A_2$ activity coincided with the major, darkly stained 28 kDa protein indicating that this band represents the phospholipase $A_2$ protein (FIG. 3).

Figure 1E:
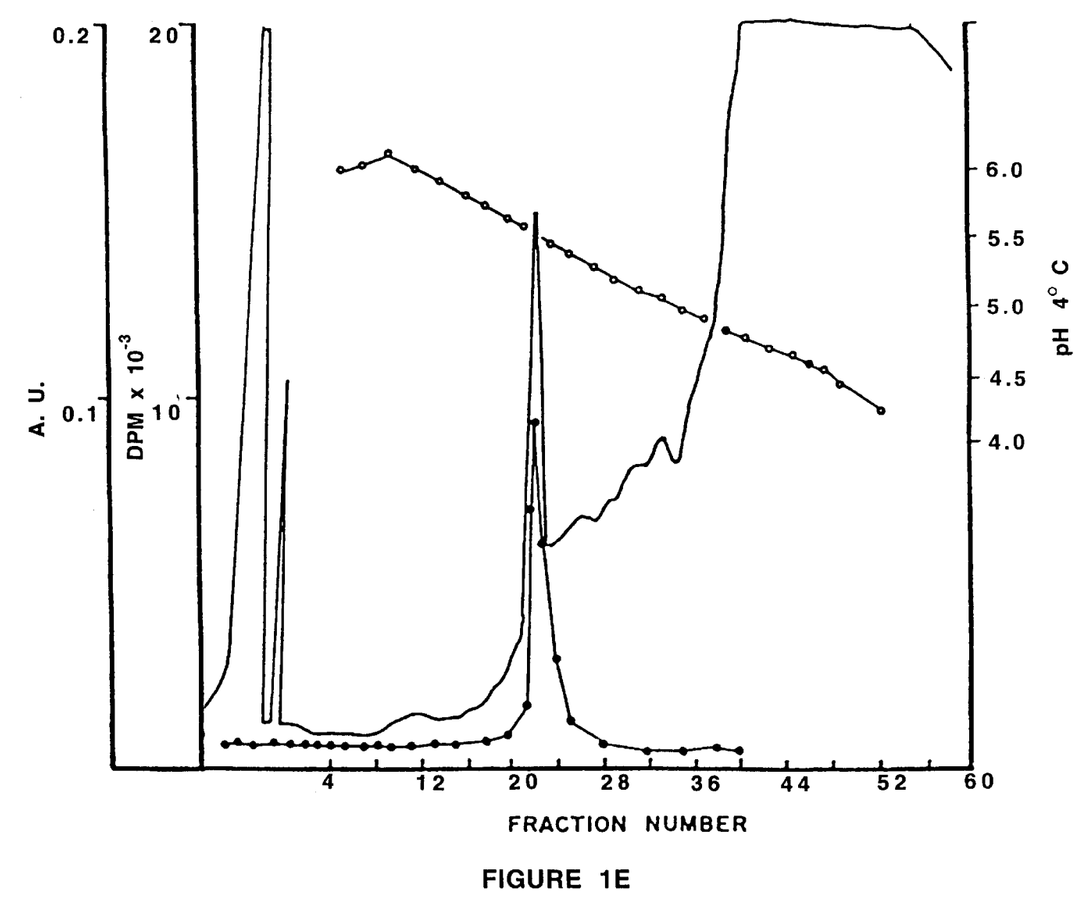

EXAMPLE 17
Chromatofocusing of Phenyl Superose Fraction Containing Calcium-independent $PLA_2$ Activity To further characterize the pI of the calcium-independent phospholipase $A_2$ activity obtained from the phenyl Superose column, chromatofocusing of this fraction was performed. Phospholipase $A_2$ activity was eluted by the generation of a shallow pH gradient which resulted in a single sharply focused peak of activity with an apparent isoelectric point of 5.6 (FIG. 1E). When the proteins were examined at various stages of purification, the intensity of the 28 kDa increased as the preparation was enriched in activity (FIG. 2).

EXAMPLE 18
Characterization of the Substrate Specificity of Purified Calcium-independent Phospholipase $A_2$ Activity Characterization of the phospholipid substrate specificity of purified kidney cytosolic phospholipase $A_2$ was performed by kinetic analysis of the Phenyl Superose hydrophobic interaction eluent which yielded more than 3,000 fold purification and a specific activity of 1.2 $\mu$m/min/mg protein.

Figure 5:
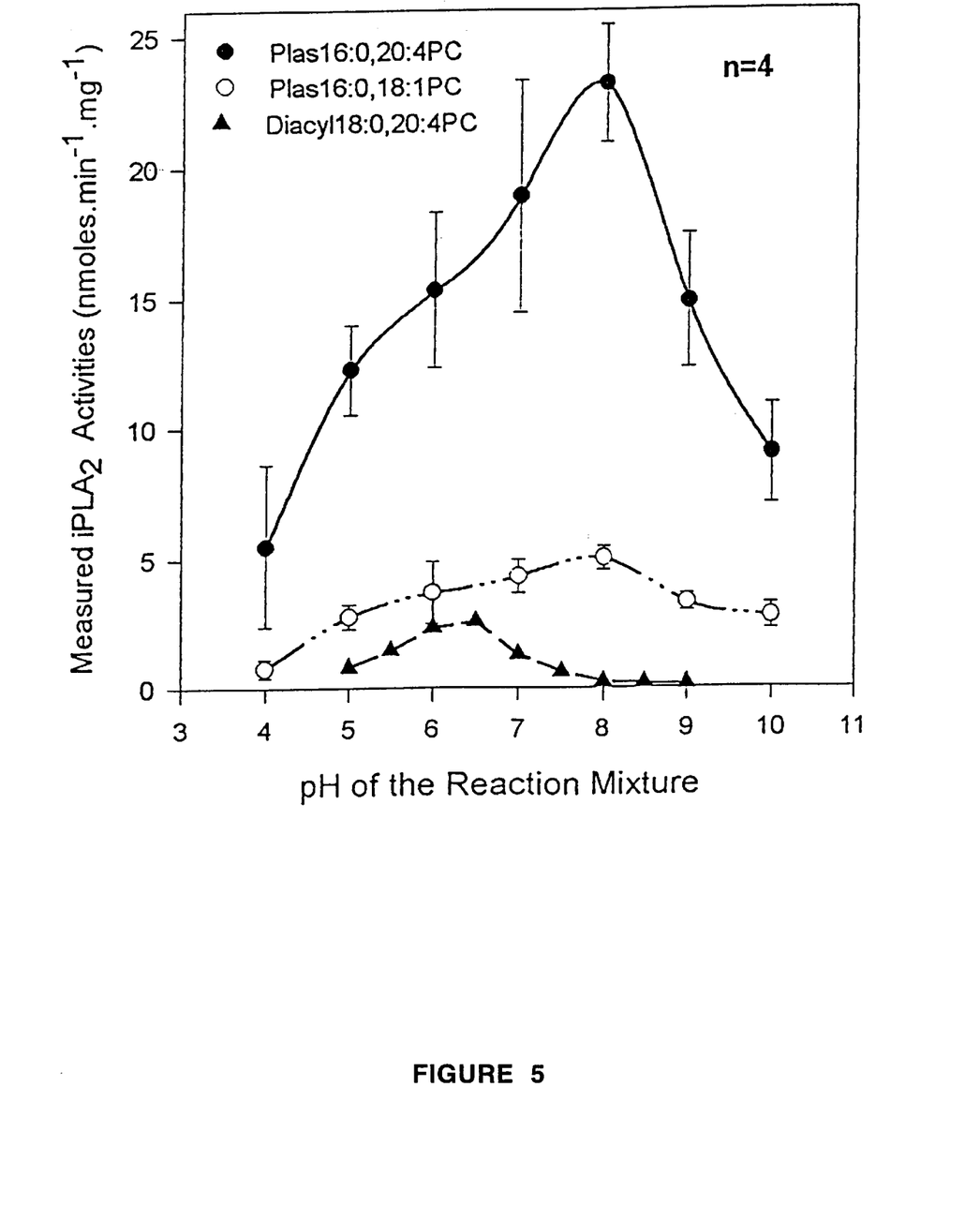
FIG. 5 shows the effect of pH and substrate specificity toward various substrates. Phospholipase $A_2$ activity from the hydrophobic interaction column was assayed with 10 µM of indicated phospholipid in the presence of buffer at various pH as described below.

Examination of the choline glycerophospholipid subclass specificity of the purified enzyme revealed that hydrolysis of plasmenylcholine was more rapid than the phosphatidylcholine. Comparison of the phospholipase $A_2$ activity utilizing phosphatidylcholine molecular species containing palmitate at the sn-1 position and either oleic or arachidonic acid at the sn-2 position as substrates demonstrated a four to five fold preference for cleavage of arachidonate over oleate (FIG. 5). To demonstrate that the purified enzyme was specific for the hydrolysis of the sn-2 position of phospholipids, lysophospholipase activity was examined. The enzyme demonstrated a small lysophospholipase activity when compared to sn-2 labeled substrates. Thus it was demonstrated that the hydrolysis of fatty acid detected in the assay was specific for the sn-2 rather than the sn-1 position.

EXAMPLE 19

Characterization of the 28 kDa Protein in the Purified Preparation

Figure 6:
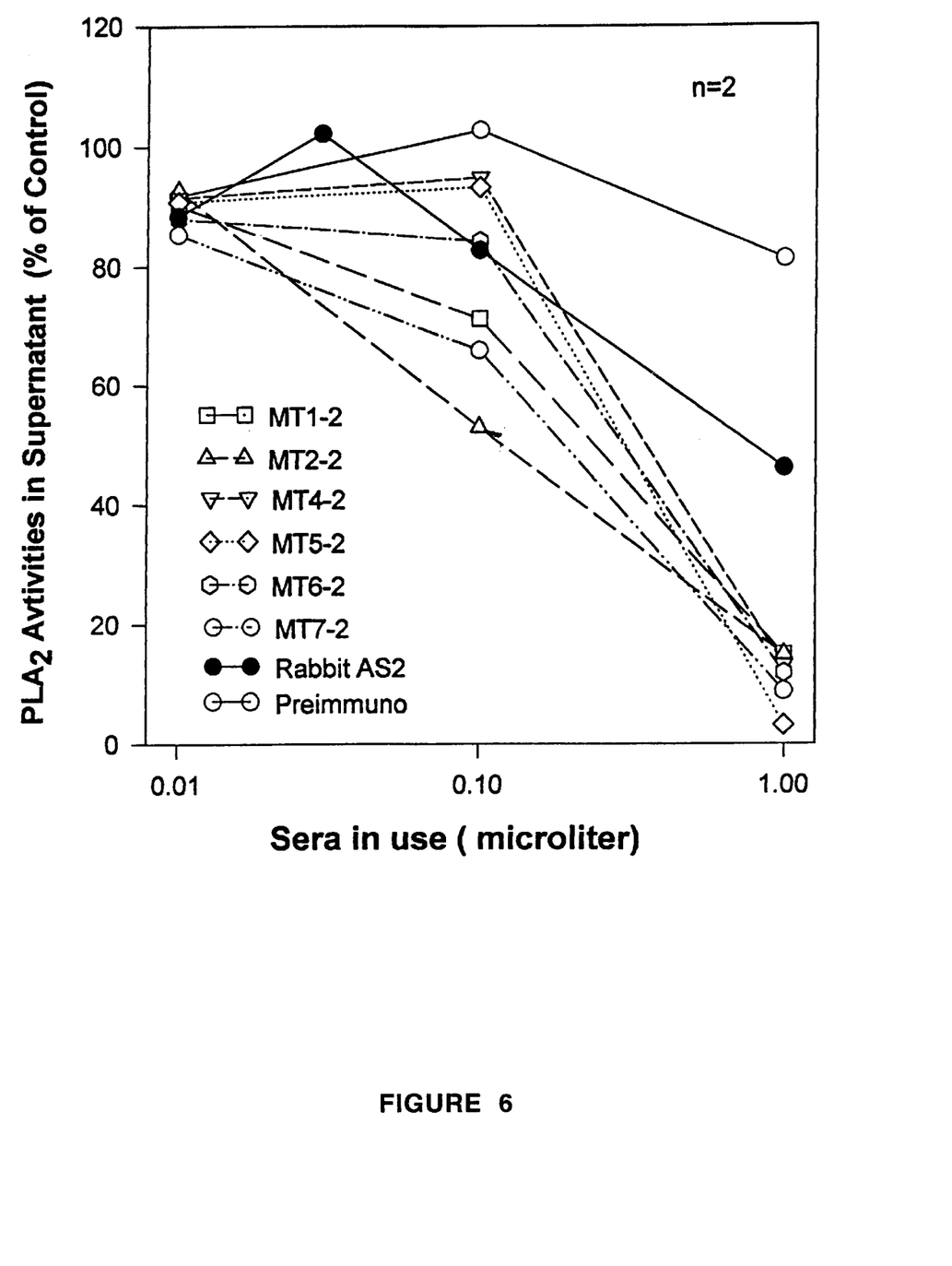
FIG. 6 shows the immunoprecipitation of calcium-independent phospholipase $A_2$ activity by a mouse polyclonal antibody raised against the 28 kDa protein.

To verify that the 28 kDa protein was indeed responsible for the phospholipase $A_2$ activity, polyclonal antibodies were raised against the rabbit kidney 28 kDa protein and tested for immunoreactivity with the phospholipase $A_2$. As shown in FIG. 6, antibodies against the 28 kDa protein were able to immunoprecipitate phospholipase $A_2$. The antibody mediated removal of calcium-independent phospholipase $A_2$ activity from the solution was accompanied by a concomitant appearance of phospholipase $A_2$ activity in the immunoprecipitate. In addition, the polyclonal mouse antibody reacted strongly with the 28 kDa band in a Western blot indicating that they were able to recognize the protein in its denatured form.

The 28 kDa protein obtained by SDS PAGE was eluted from the gel and sequenced. It was found that the amino terminal residue of the band at 28 kDa was blocked. Therefore the amino terminal residue was treated with trypsin and the reaction mixture was transferred to a polyvinylidene difluoride and carried out microsequencing. The sequence of three internal peptides was: peptide 1: ASFPQGPISGANR (SEQ ID No. 1); peptide 2: TLVNPANVTFK (SEQ ID No. 2); and peptide 3: ALIDQE (SEQ ID No. 3). A search using a protein sequence data bank indicated that there were no perfect matches of these three peptides for any known phospholipase $A_2$. Thus, this protein is pure and that this sequence likely represents part of the amino acid sequence of a novel family of calcium-independent phospholipases $A_2$.

The present invention represents the first purification of a novel calcium-independent phospholipase $A_2$ activity from rabbit kidney, which has specificity for cleavage of the sn-2 acyl linkage in diradyl glycerophospholipids. Rabbit kidney calcium-independent phospholipase $A_2$ activity was the major measurable enzyme activity in the kidney and it was in a very low abundance requiring more than a 3,200 fold purification to reach apparent homogeneity. The degree of purification of kidney calcium-independent phospholipase $A_2$ was facilitated by the use of small amounts of Triton X-100 in the buffers which helped stabilize the activity. Although this observation implies that the enzyme prefers mixed micelles over vesicles, it is also possible that the detergent stabilized or facilitated a conformational change between the enzyme and the lipid interface present during isolation.

Rabbit kidney calcium-independent phospholipase $A_2$ did not bind to the ATP-affinity column matrices in the presence or absence of Triton X-100. This property represents a major difference in the scheme of purification from the previously purified calcium-independent phospholipase $A_2$ enzymes. The major steps of the purification of the rabbit kidney calcium-independent phospholipase $A_2$ of the present invention were obtained using hydrophobic interaction columns as well as hydroxyapatite columns, suggesting that the enzyme readily interacts on a lipid water interface.

Substrate specificity of the purified protein demonstrated that rabbit kidney phospholipase $A_2$ selectively hydrolyzed plasmalogen substrates and arachydonylated glycerophospholipids. The purified polypeptide did not contain intrinsic lysophospholipase activity.

The final step of purification demonstrated the enrichment of a single 28 kDa protein on SDS PAGE visualized by coomassie blue staining. To further confirm that the molecular mass of calcium-independent phospholipase $A_2$ corresponded to this protein, this fraction was subjected to native gel electrophoresis analysis and the band that corresponded to this protein was cut. This experiment confirmed that the major protein isolated from the hydrophobic interaction column which has an estimated size of 28 kDa had indeed intrinsic calcium-indeperident phospholipase $A_2$ activity. Chromatofocusing analysis of this fraction as well as isoelectrical focusing gel again confirmed the presence of a 28 kDa protein with a pI of 5.6 with calcium-independent phospholipase $A_2$ activity. In addition, the immunoprecipitation of phospholipase $A_2$ activity by a mouse polyclonal antibody against the 28 kDa protein further confirmed that this protein is associated with calcium-independent phospholipase $A_2$ activity in the kidney.

The phospholipase $A_2$ activity purified in the present invention is unique when compared to other previously described calcium-independent phospholipase $A_2$s. The two best characterized calcium-independent phospholipase $A_2$ activities correspond to the plasmalogen-specific canine myocardial enzyme (Gross et al) and the P388D1 macrophage cell line cytosolic calcium-independent phospholipase $A_2$ recently described by Dennis. Both of these enzymes differ from the purified enzyme by the following features. First, both enzymes bind ATP-affinity matrices constituting this one, the major step of purification.

Secondly, both enzymes appear to be associated to high molecular weight complexes, the myocardial enzyme associated with a 400 kDa protein likely to be a phosphofructokinase, and the macrophage enzyme associated to a 330 kDa protein by radiation-inactivation studies. Finally, both enzymes have different molecular sizes—the myocardial one 40 kDa, and the P388D1 approximately 80 kDa. Nevertheless, the final purified form of rabbit kidney calcium-independent phospholipase $A_2$ shares some similarities with the myocardial enzyme. For example, the rabbit kidney calcium-independent phospholipase $A_2$ has a substrate preference for plasmalogen>diacyl PC and also displayed a fatty acid preference for arachidonyl>palmitoyl. Finally, the additional experiments using specific antibodies against the 28 kDa protein to immunoprecipitate the calcium-independent phospholipase $A_2$ activity demonstrate that this protein corresponds to a previously unknown family of phospholipases $A_2$.

It has recently been demonstrated that rabbit proximal tubule plasmalogens highly enriched in arachidonic acid represent the primary target for accelerated phospholipid hydrolysis during hypoxia (KI). Since the rabbit kidney cortex phospholipase $A_2$ activity purified herein has direct physical access to the proximal tubule membranes and selectively hydrolyzes plasmalogen substrate and arachydonylated glycerophospholipids, this phospholipase has the catalytic potential to hydrolyze the predominant proximal tubule phospholipid components enriched in arachidonic acid during ischemia. Accordingly, the activation of this polypeptide is expected to result in the selective release of arachidonic acid and catabolism of proximal tubule phospholipids similar to that seen during ischemia-hypoxic cell injury to the kidney. Although the mechanisms of activation and regulation of this new group of calcium-independent phospholipases $A_2$ remains unknown, future efforts to identify the molecular mechanism responsible for activation of calcium-independent phospholipase $A_2$ should provide insight into the mechanisms leading to cell death during renal ischemia.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

The following references were cited herein:
1. Dennis E. A. (1983) in The Enzymes (Boyer P. D., ed.) pp 307–353, Academic Press, New York.
2. Verheij H. M., Slotboom A. J., and de Haas G. H. (1981) Rev. Physiol. Biochem. Pharmacol. 91, 91–203.
3. Dennis E. A. (1994) *J. Biol. Chem.* 269, 13057–13060.
4. Waite M. (1987) Handbook of Lipid Research Vol. 5, The Phospholipases Plenum Press, New York.
5. Clark J. D., Milona N. and Knoff J. L. (1990) *Proc. Natl. Acad. Sci. USA* 87, 7708–7712.
6. Kramer R. M., Roberts E. F., Manetta J., and Putnam J. E. (1991) *J. Biol. Chem.* 266, 5268–5272.
7. Wolf R. A., and Gross R. W. (1985) *J. Biol. Chem.* 260, 7295–7303.
8. Hazen S. L., Stuppy R. J., and Gross R. W. (1990) *J. Biol. Chem.* 265, 10622–10630.
9. Hazen S. L., and Gross R. W. (1991) *J. Biol. Chem.* 266, 14526–14534.
10. Ackermann E. J., Kempner E. S., and Dennis E. A. (1994) *J. Biol. Chem.* 269, 9227–9233.
11. Ackermann E. J., Conde-Frieboes K., and Dennis E. A. (1995) *J. Biol. Chem.* 270, 445–450.
12. Hazen S. L., Ford D. A. and Gross R. W. (1991) *J. Biol. Chem.* 266, 5629–5633.
13. Hazen S. L. and Gross R. W. (1993) *J. Biol. Chem.* 268, 9892–9900.
14. Portilla D., Shah S. V., Lehman P. A. and Creer M. H. (1994) *J. Clin. Invest.* 93, 1609–1615.
15. Portilla D. and Creer M. H.(1995) *Kidney Int.* 47, 1087–1094.
16. Schonefeld M., Mandel L. J., Creer M., Portilla D. J Am Soc Nephrol, 5(3): 908, 1994.

---

We claim:

1. An antibody that specifically binds to a substantially pure phospholipase $A_2$ protein isolated and purified from rabbit kidney cortex, having a molecular weight of 28 kDa as determined by SDS-PAGE, is calcium independent, is cytosolic, has an internal sequence comprising:

ASFPQGPISGANR (SEQ ID No. 1);

TLVNPANVTFK (SEQ ID No. 2); and

ALIDQE (SEQ ID No. 3); and exhibits a preferential hydrolysis toward sn-2 fatty acid from diradylglycerophospholipids.

2. The antibody of claim 1, wherein said antibody is a monoclonal antibody.

3. The antibody of claim 1, wherein said antibody is a polyclonal antibody.

4. The antibody of claim 1, wherein said antibody is linked to a detectable label.

5. A hybridoma that produces the antibody of claim 2.

6. A kit for immunodection, comprising:

a container means;

the monoclonal antibody of claim 2; and an immunodetection reagent.

7. The kit of claim 6, wherein said immunodetection reagent is a detectable label linked to said antibody.

* * * * *